(12) United States Patent
Maier et al.

(10) Patent No.: US 10,709,328 B2
(45) Date of Patent: Jul. 14, 2020

(54) MAIN MODULE, SYSTEM AND METHOD FOR SELF-EXAMINATION OF A USER'S EYE

(71) Applicant: Sony Corporation, Tokyo (JP)

(72) Inventors: Andreas Maier, Erlangen (DE); Gerd Haeusler, Erlangen (DE); Aleksandra Milczarek, Erlangen (DE); Tobias Geimer, Erlangen (DE); Markus Schreiter, Erlangen (DE); Thomas Kaestner, Erlangen (DE); Florian Willomitzer, Erlangen (DE)

(73) Assignee: SONY CORPORATION, Tokyo (JP)

( * ) Notice: Subject to any disclaimer, the term of this patent is extended or adjusted under 35 U.S.C. 154(b) by 20 days.

(21) Appl. No.: 16/035,059

(22) Filed: Jul. 13, 2018

(65) Prior Publication Data

US 2019/0021588 A1  Jan. 24, 2019

(30) Foreign Application Priority Data

Jul. 19, 2017 (EP) .................................... 17182214

(51) Int. Cl.
| | |
|---|---|
| *A61B 3/113* | (2006.01) |
| *A61B 3/00* | (2006.01) |
| *A61B 3/032* | (2006.01) |
| *A61B 3/14* | (2006.01) |
| *G06F 3/01* | (2006.01) |

(52) U.S. Cl.
CPC ............ *A61B 3/113* (2013.01); *A61B 3/0041* (2013.01); *A61B 3/032* (2013.01); *A61B 3/14* (2013.01); *G06F 3/013* (2013.01)

(58) Field of Classification Search
CPC ....... A61B 3/113; A61B 3/0041; A61B 3/032; A61B 3/14; A61B 3/12; G06F 3/013; G16H 50/20; G06K 9/6217; G06K 9/6267
USPC ......................................... 351/200, 205, 209
See application file for complete search history.

(56) References Cited

U.S. PATENT DOCUMENTS

| | | | |
|---|---|---|---|
| 8,702,238 B2 | 4/2014 | Berry et al. | |
| 9,033,508 B2 | 5/2015 | Bartlett et al. | |
| 9,526,417 B1 | 12/2016 | Massetti et al. | |
| 2007/0066916 A1 | 3/2007 | De Lemos | |
| 2016/0106315 A1 | 4/2016 | Kempinski | |

FOREIGN PATENT DOCUMENTS

| | | |
|---|---|---|
| CN | 202843576 | 4/2013 |
| WO | WO 2017/108952 A1 | 6/2017 |

*Primary Examiner* — Tuyen Tra
(74) *Attorney, Agent, or Firm* — Xsensus LLP

(57) ABSTRACT

A main module for a modular system for self-examination of an eye is provided. The main module has an interface for coupling with at least one other module of the modular system and a processor. The processor is configured to perform at least one eye test algorithm by controlling the at least one other module.

20 Claims, 3 Drawing Sheets

MAIN MODULE, SYSTEM AND METHOD FOR SELF-EXAMINATION OF A USER'S EYE

TECHNICAL FIELD

The present disclosure generally pertains to main module, a system and a method for self-examination of a user's eye.

TECHNICAL BACKGROUND

Generally, it is known to perform fundus photography of the fundus of the eye for detecting eye diseases and impairments. Such photography can also be performed with consumer electronic devices, such as with a camera integrated into a smartphone.

Additionally, applications (also known as "apps"), e.g. running on a smartphone, are known which offer eye or vision tests. Typically, such tests are limited to the provided test patterns, which are observed by the user, and such tests are also limited due to feedback provided by the user, which may be unspecific, since it only describes unspecific "this is blurred" or "I do not see the dot", etc.

Although there exist techniques for self-examination of a user's eye function, it is generally desirable to improve present technologies.

SUMMARY

According to a first aspect, the disclosure provides a main module for a modular system for self-examination of an eye, the main module including an interface configured to couple with at least one other module of the modular system; and a processor configured to perform at least one eye test algorithm by controlling the at least one other module.

According to a second aspect, the disclosure provides a system for self-examination of an eye, including a main module including an interface configured to couple with at least one other module of the modular system; and a processor configured to perform at least one eye test algorithm by controlling the at least one other module; and at least one other module configured to communicate with the main module.

According to a third aspect, the disclosure provides a method for controlling a main module for a modular system for self-examination of an eye, including communicating with at least one other module coupled to the main module; and performing at least one eye test algorithm by controlling the at least one other module.

Further aspects are set forth in the dependent claims, the following description and the drawings.

BRIEF DESCRIPTION OF THE DRAWINGS

Embodiments are explained by way of example with respect to the accompanying drawings, in which.

DETAILED DESCRIPTION OF EMBODIMENTS

Figure 2:
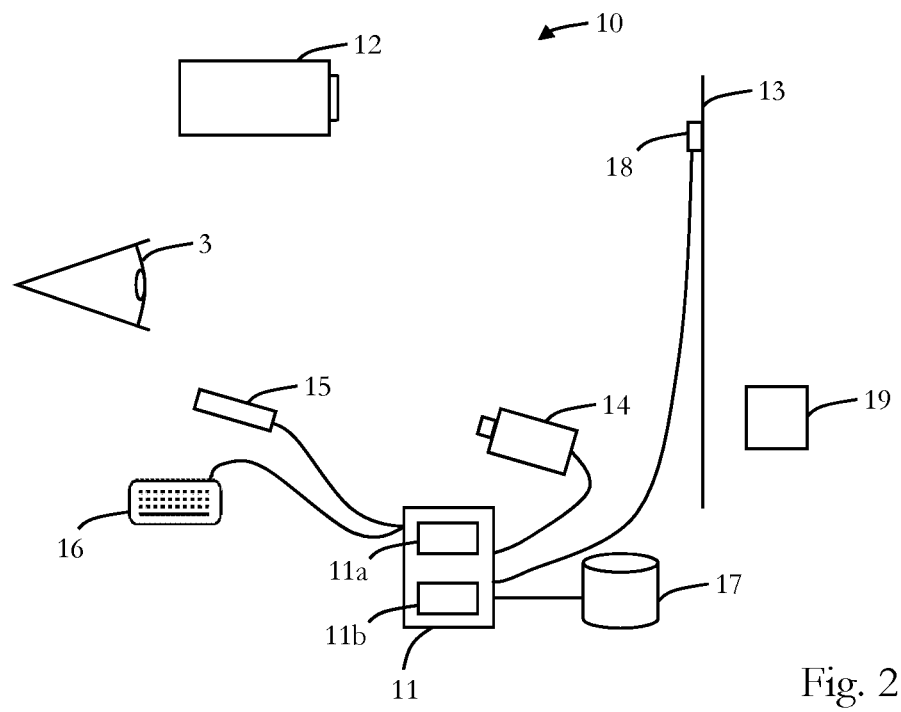
FIG. 2 illustrates a first embodiment of a system for self-examination of a user's eye.
Figure 3:
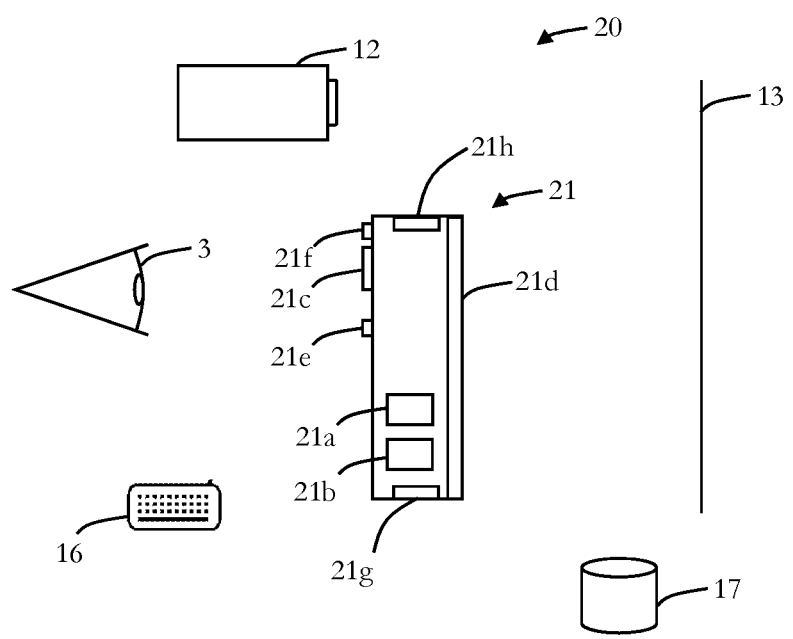
FIG. 3 illustrates a second embodiment of a system for self-examination of a user's eye.
Figure 4:
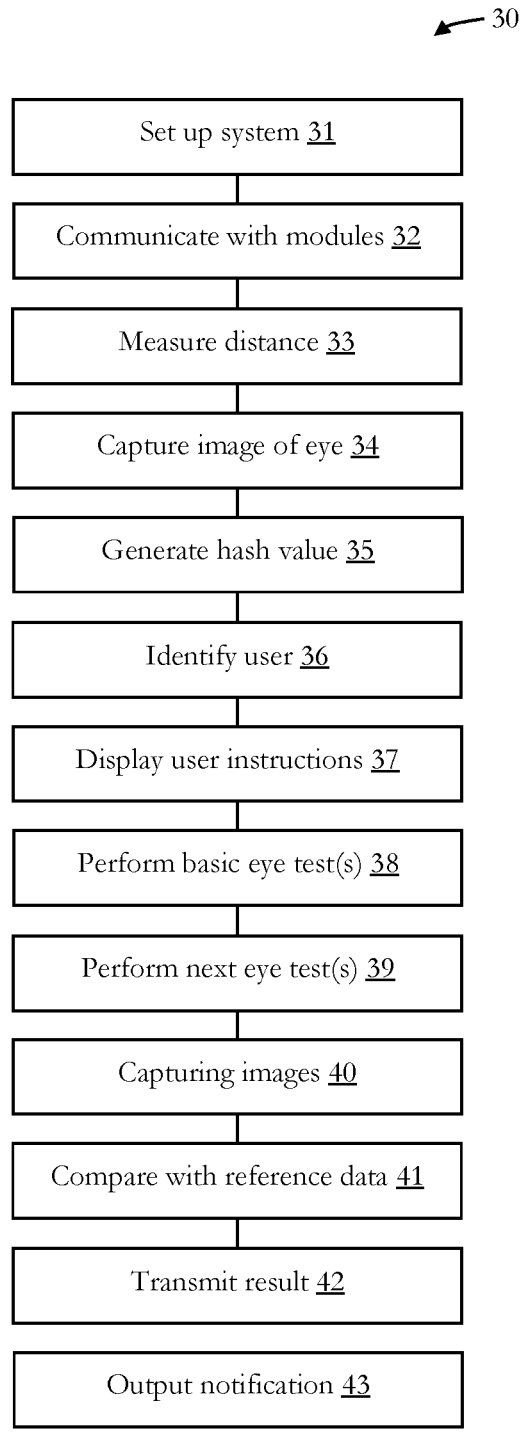
FIG. 4 illustrates a method for self-examination of a user's eye.

Before a detailed description of the embodiments under reference of FIG. 2 to FIG. 4 is given, general explanations are made.

As mentioned, generally, technologies for self-examination of a user's eye exist. Some of the embodiments, pertain to a reliable pre-diagnosis of eye diseases and impairments by providing, for example, a simple, non-expensive self-examination of the eye, which does not require the assistance presence of an ophthalmologist.

Some embodiments pertain to a main module for a modular system for self-examination of a user's eye. The main module includes an interface for (configured to) coupling (couple) with at least one other module of the modular system, and a processor configured to perform at least one eye test algorithm by controlling the at least one other module.

The modular system for self-examination may include one or more other modules than the main module, and, thus, can be selectively adapted to a specific situation for self-examination of a user, wherein the eye of the user, but also other capabilities or organs or the like of the user may be self-examined.

The interface of the main module may be configured for wire/wireless data communication with the at least one other module, with a network, with the internet, etc. Moreover, the interface may directly communicate with the other module(s) or it may indirectly communicate with the other module(s), e.g. by being directly or indirectly connected to the at least one other module. The interface may be specifically designed for communication with a specific other module or it may communicate via standard connection, e.g. local area network, wireless local area network, infrared, Bluetooth, or the like and over the associated data and communication protocols.

The coupling of the main module via the interface with the at least one other module may be performed via a standard communication protocol as used in standard communication over a network, Bluetooth, infrared or the like or it may involve a specific pairing process, which is designed for the coupling of the main module and the at least one other module.

The processor may be a microprocessor or the like and it may include multiple processors or processor cores.

The processor is configured to perform at least one eye test algorithm. Generally, the eye test algorithm may be such designed that it can perform a respective eye test without the need of having a person (doctor) or the like being involved.

Eye tests, which can be performed by an eye test algorithm, are for example: Amsler Test (for determining macula detachment, age macula degeneration); Landolt Acuity Test (for determining visual acuity, performing refraction test); Stereo Test (for determining Binocular Vision); Field of View/FOV Test (for determining central and peripheral vision impairments); Pupil Reaction Test (for determining physiological response); Eye Tracking/Movement Test (for determining eye activity); Blue Fovea Test (for providing a macula function test), Flicker Test (for determining neurological interpretation); Color Test (e.g., Ishihara Test, color blindness determination); Contrast Sensitivity (for detecting subtle visual loss when VA is normal, detachment of retina, age related macular degeneration); Laser Speckle (for determining refraction; pupil reaction); and optical illusions for diagnosis, without limiting the present disclosure to these examples.

The eye test algorithm may include user instructions with which a user is instructed to perform certain (predefined) actions, such as reading a text, looking at a pattern and trying to identify a structure, and the like, as it is generally known, for performing the respective eye test. Moreover, the eye test algorithm may use patterns for the eye test and other sensor data, which are also discussed further below.

The eye test is performed by controlling the at least one other module, which may be, for example, a projector, a distance sensor, a video camera, a microphone, a display device, a loudspeaker, a laser, or an input device or the like.

The main module may be a mobile device, e.g. a tablet pc, smartphone, personal digital assistant or the like. Hence, the main module may be moveable and may be a consumer product. The main module may include typical components, which are integrated in known mobile devices, such as memory, storage, display, touch screen, camera, mobile communication interface, etc.

In some embodiments, the at least one other module is a (data) projector and the processor is configured to control the projector to project an eye test pattern. As discussed, in some known eye tests eye test pattern are needed for performing the respective test. Hence, the main module may control the projector to project the respective eye test pattern, e.g. on a screen. Thereby, even more than one user may make a self-examination, but a group of users may look at the pattern for performing an eye test performed by the processor of the main module by performing the eye test algorithm. The data projector can be any type of projector, which is able to be project image data onto a screen.

In some embodiments, the processor is configured to perform at least a first and a second eye test algorithm subsequently. Hence, the processor is configured to perform at least two eye test algorithms, namely the first and the second eye test algorithm. The first test eye algorithm may be completed before the second eye test algorithm is performed. Thereby, different eye tests can be performed which are sensitive for different eye decreases or impairments.

In some embodiments, the second eye test algorithm is performed based on a result of the first eye test algorithm. In such embodiments, it is possible to only perform the second eye test algorithm, for example, in cases where the result of the first eye test algorithm was negative (i.e. failed), i.e. the results gives an indication for a decreases or impairment. Thereby, unnecessary eye testing may be avoided.

In some embodiments, the main module further includes a (digital) camera (e.g. based on charged-coupled-device or complementary metal oxide semiconductor technology or the like) for capturing an image of the user's eye. The processor may also be configured to perform the eye test algorithm based on the captured imaged and it may, for example, analyze the captured image in order to detect a decease or impairment.

In some embodiments, the main module may further include a display for displaying user instructions for performing the at least one eye test algorithm.

In some embodiments, as also indicated above, the at least one other module is a distance sensor for measuring a distance between a screen and the user. As mentioned above, by measuring the distance, cheating during the eye test may be prohibited, the accuracy of an eye test may be improved based on the distance information or the distance information may be needed for certain eye tests (e.g. for refraction tests or the like).

In some embodiments, the processor is further configured to perform the at least one eye test algorithm based on the measured distance.

In some embodiments, the user may give feedback to the main module, e.g. by inputting information over a touch screen of the main module or over another module, e.g. a keyboard, or over a camera which takes images of gestures made by the user, wherein in such embodiments, the processor may also be configured to perform a gesture recognition.

As mentioned, in some embodiments, a display is provided as other module, which may, for example, display eye patterns, user instructions or the like for performing the eye test algorithm under the control of the main module.

In some embodiments, the other module may be a loudspeaker for outputting, for example, user instructions or audio instructions. But, in some embodiments, the loudspeaker may be used for performing further tests, such as audiometry.

In some embodiments, the other module may be a laser, which may be used for displaying patterns or other information, for example, on a screen or even on a wall. It may be used for projecting a laser point on a screen or wall or the floor, which shall be followed by the user, etc.

In some embodiments, the other module (e.g. the digital camera) may be a video camera, which captures images of the user, the user's (eye), of the face, the hands, etc. Hence, the processor may be configured to perform, based on the captured images, a recognition of the user, face recognition, eye tracking for performing specific eye tests, gesture recognition or the like.

In some embodiments, the main module is configured to output a notification to the user, based on the result of the at least one eye test algorithm. This notification can be displayed on a display, might be output via audio output, etc., and may include that the user shall go to a doctor (ophthalmologist), hospital, etc. Moreover, information over the user, such as images of the user's eye, may be transmitted to the doctor, the hospital, a remote server, a (transportable) storage medium, etc. Also the result of the eye test algorithm may be transmitted to a remote server, the doctor, a hospital, a remote computer or the like.

In some embodiments, information of the user is made anonymous, but unique, e.g. by using bio-sensor data (eye, fingerprint, etc.) and generating a hash based on the bio-sensor data.

In some embodiments, the eye test algorithm is able to identify a decease or impairment of the eye, based on captured image data of the user's eye. This can be achieved, by an eye test algorithm which is based on a machine learning algorithm or the like, which may be trained in advance. Such eye test algorithms, which may be used for such automatic detection, may be based on at least one of the following: Feature extraction techniques, classifier techniques or deep-learning techniques. Feature extraction may be based on at least one of: Scale Invariant Feature Transfer (SIFT), Cray Level Co-occurrence Matrix (GLCM), Gaboo Features, Tubeness or the like. Classifiers may be based on at least one of: Random Forest; Support Vector Machine; Neural Net, Bayes Net or the like. Deep-learning may be based on at least one of: Autoencoders, Generative Adversarial Network, Weakly Supervised Learning, Boot-Strapping or the like.

Some embodiments pertain to a system for self-examination of a user's eye, as also mentioned above, which includes a main module as discussed herein and at least one other module configured to communicate with the main module, as discussed herein.

Hence, by providing a modular system, a mobile eye test center may be provided which can be selectively assembled, based on a respective need. Hence, the other modules can be selected as needed for specific eye tests, which have to be done and with the main module, one or more users can perform self-examination of the eye.

As mentioned, the at least one other module includes at least one of a projector, a distance sensor, a video camera, a microphone, a display device, a loudspeaker, a laser, or an input device or the like.

Moreover, the system may be connected to a remote server over a network, the internet or the like; it may be connected to a database, which, for example, stores images captured from the user (e.g. his eye). The remote server might store additional data like historic medical data of the user, medical data of the user from other sources and also reference medical data. This might provide the basis for telemedicine applications.

Some embodiments pertain to a method for controlling a main module, as described herein, for a modular system for self-examination of a user's eye, as described herein. The method includes communicating with at least one other module coupled to the main module and performing at least one eye test algorithm by controlling the at least one other module, as discussed above. As discussed, the at least one other module may be a projector and the method may further include controlling the projector to project an eye test pattern. The method may further include performing at least a first and a second eye test algorithm subsequently, as discussed, wherein the second eye test algorithm is performed based on a result of the first eye test algorithm. The method may further include capturing an image of the user's eye, displaying user instructions for performing the at least one eye test algorithm, and measuring a distance between a screen and the user, wherein the at least one eye test algorithm may be performed based on the measured distance, as discussed above. The method may further include identifying the user based on eye data.

With the main module, system and/or method described herein, the specifity, sensitivity and/or reliability of the eye-test(s) may be significantly increased by, for example, at least one additional module, e.g. providing the simultaneous observation of the eyes and the face via a camera. As discussed, with the camera, the eye movements may be tracked, the pupil size may be determined, and facial expressions/gestures may be interpreted (such as squinting, frowning, tensions, etc.) by the main module. This may be used, for example, for adapting the tests to the user's condition. Additionally, by the use of the camera or by an auxiliary distance sensor as other module, the distance to test person may be determined, as discussed. This allows for adaptable test patterns (scaling of symbols according to the intended capture size; thus cheating is prevented). More parameters, such as the voice observation, or cardiac monitoring could be included by providing corresponding modules. The sequence of the tests may also be adapted, as discussed. For example, to further investigate the result of a previous test and, for example, to exclude one or more options of interpretation of the test. Further tests may be provided to the user, based on the achieved scores or results in the previous tests.

In some embodiments, an automatic evaluation of the face gestures, eye movement and/or face-display distance is provided during the self-examination by providing corresponding modules and configuring the processor of the main module. As discussed, the combination of different test results, the eye observation and their interpretation is performed by at least one eye test algorithm performed by the processor.

In some embodiments, this allows for a multidimensional analysis of the results by algorithms via pattern recognition and provide pre-diagnostics of the eyes and a possible recommendation to visit an ophthalmologist by, for example, notifying the user, as discussed above. The wide range of available parameters may also allow to extend preliminary diagnosis to non-eye related diseases, in some embodiments.

Figure 1:
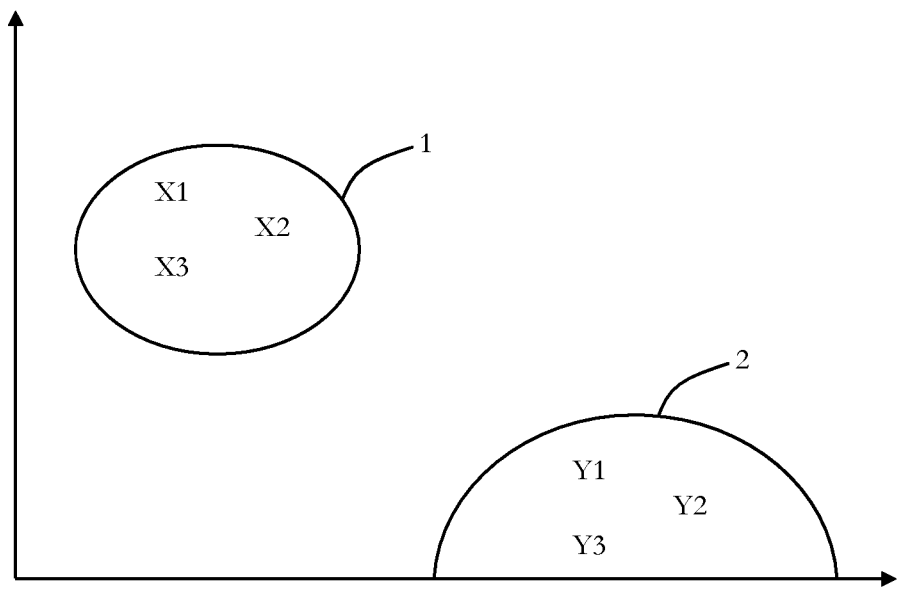
FIG. 1 illustrates a multidimensional analysis of test results of a self-examination of a user's eye.

FIG. 1 illustrates a general example for a multidimensional analysis, wherein the ordinate illustrates the type of test, such as the eye movement during the test, and the abscissa illustrates the test result (e.g. score, or the like).

FIG. 1 shows an exemplary case where a user has performed multiple tests, wherein the results of the tests are X1 to X3 and Y1 to Y3. As can be taken from FIG. 1, test results X1, X2 and X3 are located within a region 1, wherein the results Y1, Y2 and Y3 are located in a region 2. In the present case, the region 1 is indicative of a decease, e.g. Glaucoma, wherein the region 2 is indicative of normal test results. Hence, by analyzing the pattern in this multidimensional feature space, a pre-diagnosis may be performed by the at least one eye test algorithm. Moreover, FIG. 1 illustrates that the accuracy of the eye self-examination can be enhanced, in some embodiments, by performing multiple tests (which can be identical, different, or a mixture of identical and different tests).

Returning to FIG. 2, there is illustrated a first embodiment of a system 10 with a main module 11, which is a personal computer, e.g. a laptop, in this embodiment.

The system 10 for self-examination of a user's eye 3 has multiple other modules, namely a projector 12, which can project data onto a screen 13, a digital video camera 14, which captures images of the user and the user's eye 3, a microphone 15, a keyboard 16, a remote server 17 with a medical database, a distance sensor 18 and a loudspeaker 19.

The modules 12 and 14 to 19 are all connected to the main module 11 either per line or wirelessly.

The main module 11 has a processor 11a and an interface 11b. The processor 11a is configured to perform eye test algorithms for performing eye tests, as discussed herein. The interface 11b is configured to communicate with the modules 12 and 14 to 19.

The main module 11 can control the projector 12 to project images or the like, based on the eye test algorithm performed, on the screen 13, such as eye test patterns, information about the eye test, instructions to the user who performs the self-examination of the eye, etc.

The video camera 14 captures images of the user's eye 3 and the face of the user and transmits the captured images to the main module 11 for performing eye tracking of the eyes of the user and to perform face recognition. As discussed, in other embodiments, the main module 11 may also perform gesture recognition, based on the captured images.

The microphone 15 can be used for recording voice commands issued by the user, which can be used for controlling the main module 11. The main module 11 may perform speech/voice recognition, based on speech recorded by microphone 15 and transmitted to the main module 11 over the interface 11b.

The keyboard 16, which is also connected to the interface 11b of the main module 11, can be used for inputting user feedback, controlling the eye test algorithm, e.g. by manipulating a cursor projected on the screen 13, etc. Of course, in some embodiments, instead of the projector or in addition to the projector, a display may be provided for displaying respective information, eye test pattern, etc.

The distance sensor 18 measures a distance between the screen 13 and the user, e.g. the user's eye or the forehead of the user, and transmits corresponding distance information to the main module 11 over the interface 11b, such that, for example, the main module 11 can control the size of the eye test pattern to be projected onto the screen 13, based on the distance information.

The loudspeaker 18 can be controlled by the main module 11 over the interface 11b for outputting audio information, e.g. user instructions, information about the eye test, test results, scores, etc. and it may also be used for testing, e.g. audiometry.

Further sensors may be connected as other modules to the main module, such as biometric sensors (e.g. fingerprint), or sensors for determining health parameters, such as an electrocardiogram, heart rate, temperature, blood pressure, etc.

The main module 11 may receive data from the remote server 17 over the interface 11b (e.g. over a network, wirelessly, over the internet or the like), which may include reference data for comparing of test results, data which can be used for installing software on the main module 11 for performing the eye test algorithm(s), etc. The main module 11 can also transmit data to the server 17, e.g. to a database in the server, for storing user data, test results, captured images, etc. User data may be anonymized, e.g. bio-sensor data (fingerprint, iris of the eye or the like) may be used for generating a unique hash, which can be used for storing user data anonymously. Hence, in some embodiments, user data (e.g. test results, (eye) images or the like), which are generated at different points of times, may be compared to each other by the main module 11 by fetching respective data from the database in the remote server 17. This can be done, for instance, based on a hash value, which is generated based on a fingerprint.

FIG. 3 illustrates a second embodiment of a system 20 for self-examination of a user's eye 3. The same other modules as for system 10 of FIG. 2 are provided with the same reference numbers, i.e. projector 12, screen 13, keyboard 16 and remote server 17 correspond to the respective modules of FIG. 2 of system 10.

The system 20 has a main module 21, which is a smartphone in this embodiment, which has a processor 21a and an interface 21b, which have the same functionality as the processor 11a and the interface 11b of the main module of FIG. 2.

However, in the smartphone 21 a couple of other modules are integrated, and, thus, can be used accordingly, namely a digital camera 21c, a display 21d, a distance sensor 21e (e.g. time of flight camera, two cameras for stereoscopic imaging on the basis of which the distance can be determined (e.g. based on image processing), infrared light based distance sensor, sound wave based distance sensor, etc.), a flash light 21f, a microphone 21g and a loudspeaker 21h, which have the same functionality as the corresponding modules 14, 15, 18 and 19.

In this embodiment, the smartphone 21 will communicate via its interface 21b wirelessly over a network/internet with the projector 12 and the remote server 17 and with the keyboard 16 via Bluetooth.

Of course, also in this embodiment, additional modules may be added, such as a further digital camera, microphone, loudspeaker, input devices (mouse, graphic tablet, etc.), or the like.

In the following, a method 30 for self-examination of a user's eye will be discussed under reference of FIG. 4.

The method 30 starts at 31 with setting up the system for self-examination of a user's eye, such as the system 10 of FIG. 2 or the system 20 FIG. 3. In the following, without limiting the disclosure in that regard, the method 30 will be explained under reference of system 20, where the smartphone 21 is the main module. It is assumed that the screen 13, and the other modules, e.g. the projector 12 and the keyboard 16 are positioned at a given location.

The set-up procedure at 31 may include putting the smartphone 21 into a support, which holds the smartphone 21 in a predefined position with respect to the eye 3 of a user. In some embodiments, the support is adapted to support or fix two smartphones or tablet PCs, thereby also allowing stereo-vision tests, displaying instructions on a display of one smartphone and using e.g. the camera of the other smartphone, etc.

The smartphone 21 sets up a link to the projector 12 via its interface 21b, e.g. via a (wireless local area) network connection, USB connection, HDMI connection, VGA connection or the like. The smartphone 21 also sets up a Bluetooth connection to the keyboard 16 and connects to the remote server 17, e.g. over a wireless LAN and the internet.

At 32, the smartphone 21 communicates via its interface 21b with the other modules, i.e. the projector 12, the keyboard 16 and the remote server 17 and with its internal or integrated modules 21c-h for performing the following procedure.

At 33, the smartphone 21 measures a distance between the smartphone 21 and the eye 3 of the user with the distance sensor 21e. The measurement of the distance can be performed once or it can be performed on a regular basis (e.g. periodically, such as every second, every 10 seconds, etc.) or it can be (nearly) performed continuously.

Moreover, also the distance, between the user and the screen 3 can be measured, e.g. by instructing the user over audio/visual instructions (e.g. via its loudspeaker 21h/display 21d) to hold the smartphone 21 in front of his face and aligning it accordingly, such that the distance sensor 21e can measure the distance between the eye 3 of the user and the screen 13. Hence, in some embodiments, two distance measurement values may be provided, namely for the distance between the smartphone 21 and the eye 3 of the user and for the distance between the eye 3 of the user and the screen 13.

At 34, the smartphone 21 controls the digital camera 21c to capture an image of the eye 3, generates eye data and generates a hash value based on the eye data at 35.

For identifying the user at 36, the hash value is transmitted to the remote server 17, where a database is located including multiple hash values of different users and associated previous self-examination results. By comparing the hash value generated at 34 and the hash values in the database, the user can be identified and the associated previous self-examination results and other information of the identified user can be fetched from the database from the remote server 17. By using the hash value generated based on the eye data, the user information can be anonymously stored in the database on the remote server.

At 36, user instructions are displayed on the display 21d and/or on the screen 13 by controlling the projector 12 accordingly and, at 37, a first, in this embodiment basic eye test is performed by performing a respective basic eye test algorithm, as discussed above. The basic eye test algorithm may be stored on the smartphone 21 and/or it can be downloaded from the remote server 17.

As also mentioned above, numerous tests for a great variety of impairments and even diseases may be implemented. Such tests may be at least one of (see also above): Amsler Test, Landolt Acuity Test, Stereo Test, Field of View/FOV Test, Pupil Reaction, Eye Tracking/Movement, Blue Fovea, Flicker Test, Color Test, Contrast Sensitivity, Laser Speckle, Optical illusions for diagnosis, etc.

After performing a basic test (or a set of basic tests), further tests are provided to the user based on the previously achieved scores or results at 38 (as also discussed above).

Hence, only relevant tests are performed at 38, while others are excluded, since, for example, they do not make any sense for the specific user. For instance, specific refraction tests may only be performed when a basic test yielded that the user has a decreased vision, which can be detected, e.g. displaying respective eye test patterns on the screen 13 (based on the distance between the eye 3 and the screen 13) and asking the user to input the letters, numbers and/or symbols, which the user can determine, as it is generally known. The input can be performed over the keyboard 16 and/or over the microphone 21$g$ and/or the touch display 21$d$ of the smartphone.

The tests can be classified into certain categories (based on eye diseases, impairments, etc.). The basic set of tests may cover each category.

The tests needed, may be upgraded upon medical requirements and or/test scores and results of the tests performed. Also, the upgrade may be performed by downloading respective eye test algorithms from the remote server 17.

In this embodiment, the specifity, sensitivity and reliability of the test is significantly increased by at least one additional modality, i.e. the simultaneous observation of the eyes and the face via the digital camera 21$c$ of the smartphone by capturing images at 40.

By capturing images with the digital camera 21$c$ at 40, the smartphone 21 tracks eye movements, e.g. for Parkinson disease, Glaucoma, determines the pupil size, and interprets facial expressions/gestures. These additional parameters can be used for diagnosis.

Of course, the display of user instructions at 37 and the capturing of images 40 as well as the eye tracking, face/gesture recognition, etc. may also performed during the eye tests.

Moreover, as discussed, the distance to the user is determined, which allows for adaptable test patterns, as also discussed above, such that symbols according to the intended capture size can be adapted based on the distance, and, thus, cheating the tests may be prevented.

Additionally, further parameters, such as the voice observation over the microphone 21$g$, or cardiac monitoring with further external sensors (additional modules) may be included. These parameters, together with the eye tests may allow for preliminary diagnosis to non-eye related diseases.

In the present embodiment, it is assumed that the remote server is located at a different location, but the disclosure is not limited thereto, but the remote server may also be at the location where the self-examination of the eye is performed. Moreover, the database and other information described as being stored on the remote server may be distributed among different computers.

Moreover, in the present embodiment, the method 30 is performed by the smartphone 21 (its processor 21$a$), but the present disclosure is not limited thereto, but parts of method 30 or even the whole method 30 may be performed on one or more other computers, which are located at the location of self-examination and/or which may be located remotely. For instance, in some embodiments, the a controlling and evaluation unit for controlling and evaluating the eye tests (algorithms) may be implemented by a computer which is provided at the location of the self-examination and/or which may be located remotely. In such embodiments, the smartphone 21 is basically used for capturing images, user inputs, controlling other modules (e.g. projector) and outputting user instructions, wherein the eye test algorithm(s) itself is executed by the control and evaluation unit. Of course, also in such embodiments, the functionality and the parts of the method 30 which are executed may be distributed among different components, i.e. the main module (smartphone 21), and another computer or computers which are in the local network or which are remotely located.

As discussed, for the tests, a multidimensional feature space for the test results may be used for performing a pre-diagnosis of eye diseases by means of pattern recognition algorithms. This may involve an automatic evaluation of the face gestures, eye movement and face-display distance during the self-examination, such that the combination of different test results, the eye observation and their interpretation forms a multidimensional feature space. As discussed under reference of FIG. 1, if the user develops a disease, the location of the test result will move from normal towards pathology, if the test is a good predictor of the disease under consideration. Thus, by performing the above described multidimensional analysis of the results via pattern recognition algorithms, pre-diagnostics and a possible recommendation to visit an ophthalmologist may be provided. The pattern recognition can also exploit additional measurements, including but not limited to distance measurements gained by the distance sensor. Moreover, temporal changes of the features can be analyzed, if the eye test is performed on a regular base (e.g. weekly or monthly). This may help to monitor, e.g. eye diseases or a therapy process.

As also discussed above, during the test, for example, test pictures are displayed on the device display 21$d$ and/or are projected onto the planar screen 13. If big patterns are used, which are projected on a big screen, many of the tests can be performed by a big audience simultaneously.

As discussed, during the user performs the eye tests, interactive feedback is given to the system, e.g. via the keyboard 16, the display touchscreen of the smartphone, via voice commands, gesture or the like, wherein, simultaneously, the digital camera 21$c$ observes the face and eyes.

At 41, which may also be performed during the test(s) at 38 and/39, the test results are compared to medical reference data, which may be fetched, as discussed above, from the database from the remote server 17.

For example, if the patient develops an eye disease at a later point in time, the data that was obtained during the screening process earlier can be used to identify biomarkers that are able to predict a certain eye disorder. For instance, neurological disorders like Parkinson might be identifiable using cues from eye motion, speech or other bio signals. Also, other neurodegenerative diseases affect the retina, which may also be considered as a part of the brain, and, thus, influence visual perception, which may be detected based on the tests and/or based on comparing currents test results with previous test results, i.e. reference data.

Furthermore, at 42, test results can be transmitted digitally to a hospital and/or a doctor's office in a tele medical workflow and/or to the remote server 17 for being stored in the (anonymous) user profile.

At 43, a notification may be outputted, e.g. displayed on the screen 13, the display 21$d$ or may be outputted via audio (e.g. loudspeaker 21$h$) to the user for informing about the test, e.g. that the user shall visit an ophthalmologist or that no further action is required, since no indication for a decease or impairment is found.

In some embodiments, the tests, e.g. the order and the type of tests, follow a screening protocol. If an individual user is tested, several batch tests can be selected, i.e. short test (less than 5 min) or the extensive test (if a problem is suspected). As the evaluation is done in real time during or right after the test, additional test protocols can be launched if a specific problem is suspected. Doing so, users can be hinted on specific diseases and transferred to an ophthalmologist by informing the user accordingly, e.g. at 43.

In some embodiments, test results and other information may also be transmitted to a research institute for obtaining experimental data that can be used for clinical research and potentially more accurate screening and/or prediction of eye disorders.

In some embodiments, feedback to the user can provide comparison data to population health data that allows to rank the user's performance with the general population.

In some embodiments, at least one of the tests can be incorporated in a game, such that, for example, children perform them in a playful way. Examples are posing exams as challenge to the child and ask the child to complete the task as fast as possible, award points for completed exams, and light music or animations of well-known characters as reward, e.g. "solve the puzzle for Mickey Mouse" or the like.

As indicated above, in some embodiments, one of the modules is a (mobile) projector that is able to dock to a tablet PC (main module). With the screen on the tablet, the projector/eye test center can be positioned, such that a projected calibration pattern is displayed correctly for the eye test. In another embodiment, at least one of the modules including the main module is implemented as a dockable sensor system that mainly faces the user and displays patterns on, for example, the display of tablet PC or smartphone or the like. In some embodiments, at least one module including the main module includes a head-mount that fixes the position of the person under examination. In some embodiments, at least one module including the main module includes a head mounted display.

As discussed, some embodiments provide a reliable self-examination of the eye. Moreover, in particular due to the modularity of the system, the system is scalable in some embodiments, such that it can be realized, for example, as mobile device or as a stationary device. While the mobile device can be provided to anyone, the stationary system can be provided to opticians, practices, etc. In some embodiments, the system can operate on already existing smartphone hardware and does not require additional hardware, as discussed above. In some embodiments, the system is upgradeable with additional tests and eye observation methods via algorithms. It can also be extended by low-cost hardware add-ons such as a laser and other hardware extensions. As discussed, in some embodiments, the system can connect to a database to store the user's results, compare it to other data and the data can also be shared and reviewed by an ophthalmologist. In some embodiments, the user instructions are outputted to the user based on a user friendly (graphical user) interface and is simple to use, such that, for example, no prior knowledge is needed. In some embodiments, also audio guidance can be provided by the system to guide the user through the tests. As discussed, the main module and/or the system may be multifunctional. In some embodiments, as discussed, the test results and eye-observations create a multidimensional parameter space, which allows for a better reliability and future extensions of applications. In some embodiments, the disclosure provides a low-cost user-to-display measure, which ensures the intended/appropriate test execution. In some embodiments, the test results are accessible to the user and/or to an ophthalmologist.

Hence, some embodiments provide at least one of: Additionally modality to observe the eyes and face during eye tests; reliability, specifity, sensitivity of the pre-diagnosis may be increased; may have low cost, e.g. the main module may be a consumer product; low level hardware may be used, e.g. main module may be a smartphone, such that no additional hardware cost may arise; may be upgradeable, via algorithms and additional hardware, and more tests, which may be downloadable from a remote server, installable from a storage medium, or the like; may ensure intended/appropriate test execution through low cost user to display distance measure; multidimensional parameter space may allow for better reliability; and pre-diagnosis of eye related and non-eye related diseases through analysis of the multidimensional feature space via eye test algorithm(s).

The methods as described herein are also implemented in some embodiments as a computer program causing a computer and/or a processor and/or a module and/or a system to perform the method, when being carried out on the computer and/or processor and/or a module and/or a system. In some embodiments, also a non-transitory computer-readable recording medium is provided that stores therein a computer program product, which, when executed by a processor, such as the processor described above, causes the methods described herein to be performed.

It should be recognized that the embodiments describe methods with an exemplary ordering of method steps. The specific ordering of method steps is however given for illustrative purposes only and should not be construed as binding. For example, the ordering of 33 to 42 in the embodiment of FIG. 4 may be exchanged. Other changes of the ordering of method steps may be apparent to the skilled person.

All units and entities described in this specification and claimed in the appended claims can, if not stated otherwise, be implemented as integrated circuit logic, for example on a chip, and functionality provided by such units and entities can, if not stated otherwise, be implemented by software.

In so far as the embodiments of the disclosure described above are implemented, at least in part, using software-controlled data processing apparatus, it will be appreciated that a computer program providing such software control and a transmission, storage or other medium by which such a computer program is provided are envisaged as aspects of the present disclosure.

Note that the present technology can also be configured as described below.

(1) A main module for a modular system for self-examination of an eye, the main module including:
an interface configured to couple with at least one other module of the modular system; and
a processor configured to:
perform at least one eye test algorithm by controlling the at least one other module.

(2) The main module of (1), wherein the main module is a mobile device.

(3) The main module of (1) or (2), wherein the at least one other module is a projector and wherein the processor is configured to control the projector to project an eye test pattern.

(4) The main module of anyone of (1) to (3), wherein the processor is configured to perform at least a first and a second eye test algorithm subsequently.

(5) The main module of (4), wherein the second eye test algorithm is performed based on a result of the first eye test algorithm.

(6) The main module of anyone of (1) to (5), further including a camera for capturing an image of the eye.

(7) The main module of anyone of (1) to (6), further including a display configured to display user instructions for performing the at least one eye test algorithm.

(8) The main module of anyone of (1) to (7), wherein the at least one other module is a distance sensor for measuring a distance between a screen and a user.

(9) The main module of (8), wherein the processor is further configured to perform the at least one eye test algorithm based on the measured distance.

(10) The main module of anyone of (1) to (8), wherein the processor is further configured to transmit a result of the eye test algorithm to a remote computer and/or a doctor.

(11) A system for self-examination of an eye, including:
a main module, in particular according to anyone of (1) to (10) including:
an interface configured to couple with at least one other module of the modular system; and
a processor configured to:
perform at least one eye test algorithm by controlling the at least one other module; and
at least one other module configured to communicate with the main module.

(12) The system of (11), wherein the at least one other module is a projector, a distance sensor, a video camera, a microphone, a display device, a loudspeaker, a laser, or an input device.

(13) A method for controlling a main module for a modular system for self-examination of an eye, including:
communicating with at least one other module coupled to the main module; and
performing at least one eye test algorithm by controlling the at least one other module.

(14) The method of (13), wherein the at least one other module is a projector and wherein the method further comprises controlling the projector to project an eye test pattern.

(15) The method of (13) or (14), further including performing at least a first and a second eye test algorithm subsequently.

(16) The method of (15), wherein the second eye test algorithm is performed based on a result of the first eye test algorithm.

(17) The method of anyone of (13) to (16), further including capturing an image of the eye.

(18) The method of anyone of (13) to (17), further including displaying user instructions for performing the at least one eye test algorithm.

(19) The method of anyone of (13) to (18), further including measuring a distance between a screen and a user.

(20) The method of (19), wherein the at least one eye test algorithm is performed based on the measured distance.

(21) The method of anyone of (13) to (20), further including identifying a user based on eye data.

(22) The method of anyone of (13) to (21), further including transmitting a result of the eye test algorithm to a remote computer and/or a doctor.

(23) A computer program comprising program code causing a computer to perform the method according to anyone of (13) to (22), when being carried out on a computer.

(24) A non-transitory computer-readable recording medium that stores therein a computer program product, which, when executed by a processor, causes the method according to anyone of (13) to (22) to be performed.

(25) A main module for a modular system for self-examination of an eye, the main module including:
interface means for coupling with at least one other module of the modular system; and
processing means for performing at least one eye test algorithm by controlling the at least one other module.

(26) A system for self-examination of an eye, including:
a main module, in particular according to anyone of (1) to (10) including:
interface means for coupling with at least one other module of the modular system; and
processing means for performing at least one eye test algorithm by controlling the at least one other module; and
at least one other module configured to communicate with the main module.

(27) A computer program comprising program code causing a computer to function as
interface means for coupling with at least one other module of the modular system; and
processing means for performing at least one eye test algorithm by controlling the at least one other module.

(28) A non-transitory computer-readable recording medium that stores therein a computer program product, which, when executed by a processor, causes the computer to function as
interface means for coupling with at least one other module of the modular system; and
processing means for performing at least one eye test algorithm by controlling the at least one other module.

(29) A method for controlling a main module for a modular system for self-examination of an eye, including:
step of communicating with at least one other module coupled to the main module; and
step of performing at least one eye test algorithm by controlling the at least one other module.

The invention claimed is:

1. A main module for a modular system for self-examination of an eye, the main module comprising:
an interface configured to couple with at least one other module of the modular system; and
a processor configured to:
perform a pre-diagnosis with a first eye test algorithm, the first test algorithm being a basic test, by controlling the main module and at least one other module, the main module being a mobile device, and
perform a second eye test algorithm, subsequently, the second eye test algorithm being downloaded from a remote server and performed in response to a result of the first eye test algorithm.

2. The main module of claim 1, wherein the at least one other module is a projector and wherein the processor is configured to control the projector to project an eye test pattern.

3. The main module of claim 1, further comprising a camera for capturing an image of the eye.

4. The main module of claim 3, wherein the processor is further configured to track eye movement and interpret facial expressions and gestures based on captured image by the camera.

5. The main module of claim 4, wherein the processor is further configured to perform diagnosis of eye disease according to the result of the first eye test algorithm, the second eye test algorithm, and the captured image.

6. The main module of claim 1, further comprising a display configured to display user instructions for performing the at least one eye test algorithm.

7. The main module of claim 1, wherein the at least one other module is a distance sensor for measuring a distance between a screen and a user.

8. The main module of claim 1, wherein the processor is further configured to transmit a result of the eye test algorithm to a remote computer.

9. The main module of claim 1, wherein at least one of the first and the second eye test algorithm is incorporated in a game application performed on the main module.

10. A system for self-examination of an eye, comprising:
a main module including:
an interface configured to couple with at least one other module of the modular system; and
a processor configured to:
perform a pre-diagnosis with a first eye test algorithm, the first test algorithm being a basic test, by controlling the main module and at least one other module, the main module being a mobile device, and
perform a second eye test algorithm, subsequently, the second eye test algorithm being downloaded from a remote server and performed in response to a result of the first eye test algorithm; and
at least one other module configured to communicate with the main module.

11. The system of claim 10, wherein the at least one other module is a projector, a distance sensor, a video camera, a microphone, a display device, a loudspeaker, a laser, or an input device.

12. A method for controlling a main module for a modular system for self-examination of an eye, comprising:
communicating with at least one other module coupled to the main module; and
performing a pre-diagnosis with a first eye test algorithm, the first test algorithm being a basic test, by controlling the main module and at least one other module, the main module being a mobile device, and
performing a second eye test algorithm, subsequently, the second eye test algorithm being downloaded from a remote server and performed in response to a result of the first eye test algorithm.

13. The method of claim 12, wherein the at least one other module is a projector and wherein the method further comprises controlling the projector to project an eye test pattern.

14. The method of claim 12, further comprising capturing an image of the eye.

15. The method of claim 14, further comprising performing diagnosis of eye disease according to the result of the first eye test algorithm, the second eye test algorithm, and the captured image.

16. The method of claim 12, further comprising displaying user instructions for performing the at least one eye test algorithm.

17. The method of claim 12, further comprising measuring a distance between a screen and a user.

18. The method of claim 17, wherein the at least one eye test algorithm is performed based on the measured distance.

19. The method of claim 12, further comprising identifying a user based on eye data.

20. The method of claim 12, wherein at least one of the first and the second eye test algorithm is incorporated in a game application performed on the main module.

* * * * *